(12) United States Patent
Kobayashi et al.

(10) Patent No.: US 6,565,210 B2
(45) Date of Patent: May 20, 2003

(54) OCULAR OPTICAL CHARACTERISTIC MEASURING APPARATUS

(75) Inventors: Katsuhiko Kobayashi, Tokyo (JP); Toshifumi Mihashi, Tokyo (JP)

(73) Assignee: Kabushiki Kaisha Topcon (JP)

(*) Notice: Subject to any disclaimer, the term of this patent is extended or adjusted under 35 U.S.C. 154(b) by 0 days.

(21) Appl. No.: 09/915,170

(22) Filed: Jul. 25, 2001

(65) Prior Publication Data

US 2002/0126257 A1 Sep. 12, 2002

(30) Foreign Application Priority Data

Jul. 28, 2000 (JP) .......................... 2000/229923

(51) Int. Cl.⁷ ................................. A61B 3/10
(52) U.S. Cl. ................... 351/214; 351/215; 351/221
(58) Field of Search ............................. 351/211, 212, 351/214, 215, 221, 237, 238, 239, 240, 243, 205

(56) References Cited

U.S. PATENT DOCUMENTS 5,546,142 A * 8/1996 Kobayashi .................. 351/237

* cited by examiner

*Primary Examiner*—George Manuel
(74) *Attorney, Agent, or Firm*—Baker Botts LLP

(57) ABSTRACT

An ocular optical characteristic measuring apparatus measures light intensity distribution in a target image projected on the fundus of an eye and determines the ocular optical characteristic of the eye on the basis of the light intensity distribution. A light-projecting optical system projects light emitted by a light source on the eye to form a target image on the fundus of the eye, a light-receiving optical system focuses reflected light reflected by the fundus to form a target image on a photoelectric device. An arithmetic unit determines a light intensity distribution in the target image formed on the photoelectric device on the basis of an image signal provided by the photoelectric device and estimates the optical characteristic of the eye from the light intensity distribution in the target image. Substantially all scatter-reflected light is removed from the reflected light reflected by the fundus of the eye and substantially only regularly reflected light regularly reflected by the fundus of the eye is transmitted to the photoelectric device.

4 Claims, 4 Drawing Sheets

OCULAR OPTICAL CHARACTERISTIC MEASURING APPARATUS

BACKGROUND OF THE INVENTION

The present invention relates to an ocular characteristic measuring apparatus capable of measuring a light-intensity distribution characteristic of a target image formed on a fundus of an eye and of determining the ocular optical characteristic of the eye on the basis of the measured light-intensity distribution characteristic.

When measuring the ocular optical characteristic of an eye by a conventional ocular optical characteristic measuring apparatus, a target image is formed on the fundus of the eye, a reflected target image is formed on a photoelectric device by reflected light, light-intensity distribution on the reflected target image is measured, and the point spread on the eyeball indicating the optical characteristic of the eye is determined on the basis of the measured data.

The light-intensity distribution on the target image measured by this conventional ocular optical characteristic measuring apparatus indicates the point spread on the ocular optical system of the eye. The reflected light from the image travels through the ocular optical system again and fall on the photoelectric device. Therefore, it has been thought that the light-intensity distribution in the target image formed on the photoelectric device can be expressed by the superposition integration of the point spread.

When measuring the ocular optical characteristic of the eye by the conventional ocular optical characteristic measuring apparatus, target light projected on the fundus reach not only the surface of the fundus but also a part of the fundus slightly below the surface of the fundus and the light is scattered and reflected to cause the so-called "blurred reflection".

The light reflected in a blurred reflection mode by the fundus affect the light-intensity distribution in the target image formed on the photoelectric device. Consequently, the light-intensity distribution in the target image formed on the photoelectric device does not represent accurately the superposition integration of the point spread in the ocular optical system and hence the point spread in the ocular optical system cannot be calculated exactly on the basis of only the measured light-intensity distribution.

Therefore, the development of an ocular optical characteristic measuring apparatus capable of preventing scatter-reflected light reflected by the fundus in a blur reflection mode from falling on a photoelectric device, of forming a target image on the photoelectric device only by light regularly reflected by the fundus surface and preventing the effect of unmeasurable blur reflection particular to the eye on the measurement was strongly desired.

SUMMARY OF THE INVENTION

According to the present invention, a projection optical system projects light emitted by a light source on the fundus of an eye to form a target image on the fundus. A light receiving optical system guides reflected light reflected from the fundus to a photoelectric device to form a target image on the photoelectric device and measures a light-intensity distribution in the target image formed on the photoelectric device according to a signal from the photoelectric device to determine the ocular optical characteristic of the eye. Substantially all scatter-reflected light is removed from the reflected light reflected by the fundus of the eye.

DETAILED DESCRIPTION OF THE PREFERRED EMBODIMENTS

Embodiments of the present invention will be described in detail with reference to drawings as below.

Principle of the First Embodiment

Figure 1:
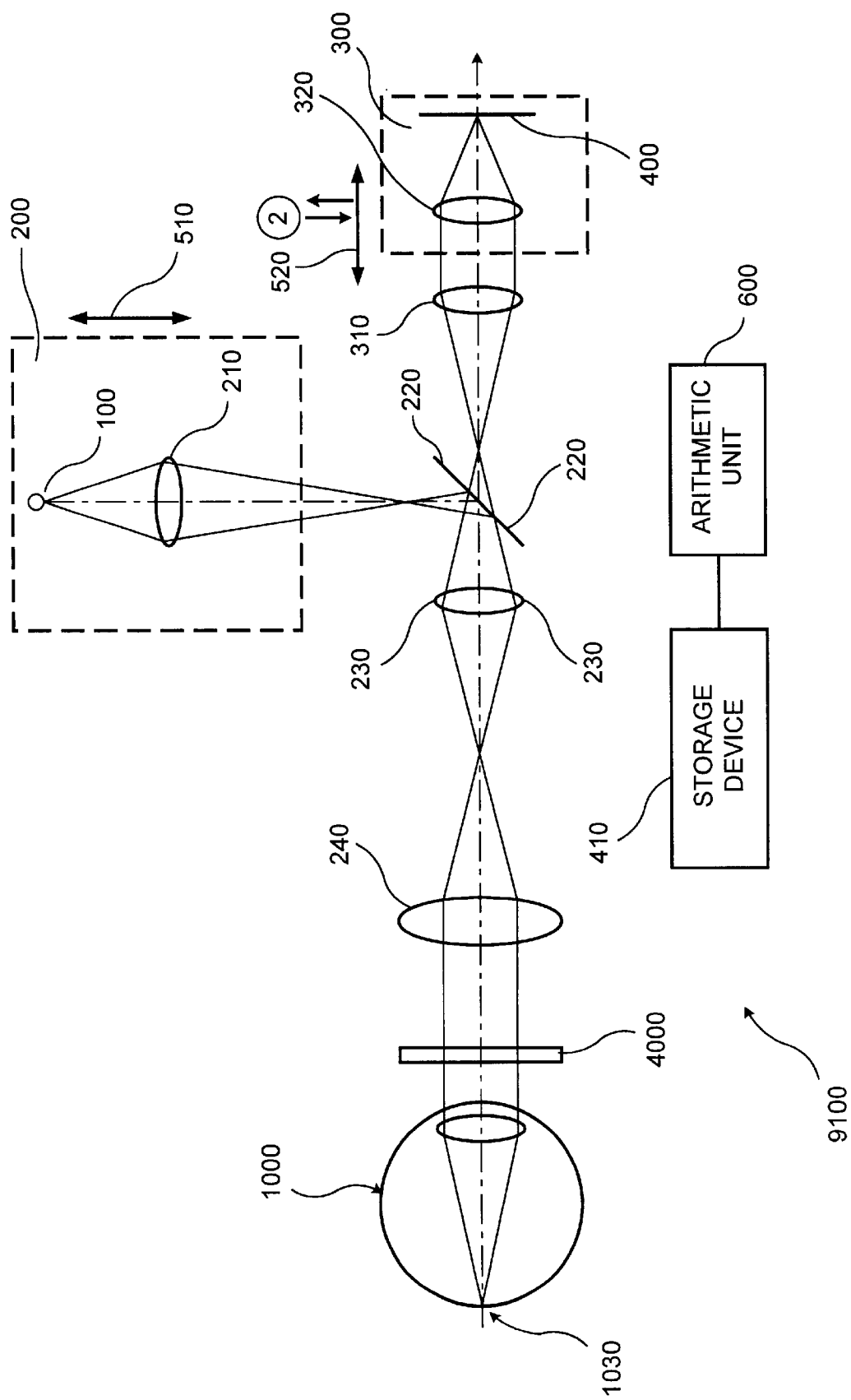
FIG. 1 is a diagrammatic view of an ocular optical characteristic measuring apparatus in a first embodiment according to the present invention.
Figure 2:
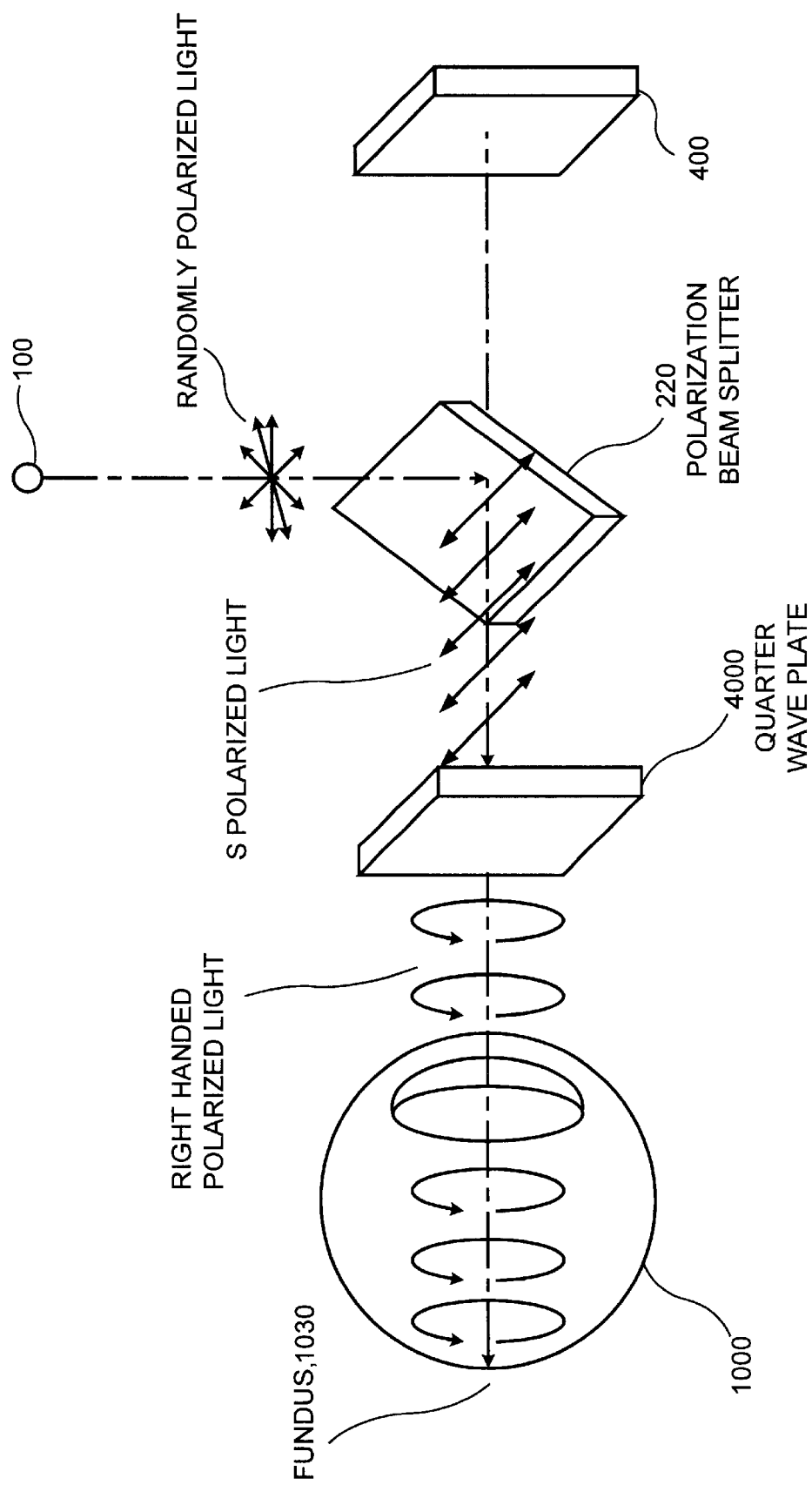
FIG. 2 is a diagrammatic view of assistance in explaining the principle of the ocular optical characteristic measuring apparatus shown in FIG. 1.

FIG. 2 is a diagrammatic view of assistance in explaining the principle of the first embodiment and a light projecting method by which an ocular optical characteristic measuring apparatus 9100 in a first embodiment according to the present invention projects light on the fundus 1030 of an eye. A polarization beam splitter 220 reflects only first linearly polarized light polarized in a first direction of polarization, i.e., S-polarized light, included in randomly polarized light emitted by a light source 100. The reflected first linearly polarized light fall on a quarter-wave plate 4000.

The quarter-wave plate 4000 is set at an azimuth angle of +45° to the S-polarized light to project right-handed polarized light on the fundus 1030 of an eye.

Figure 3:
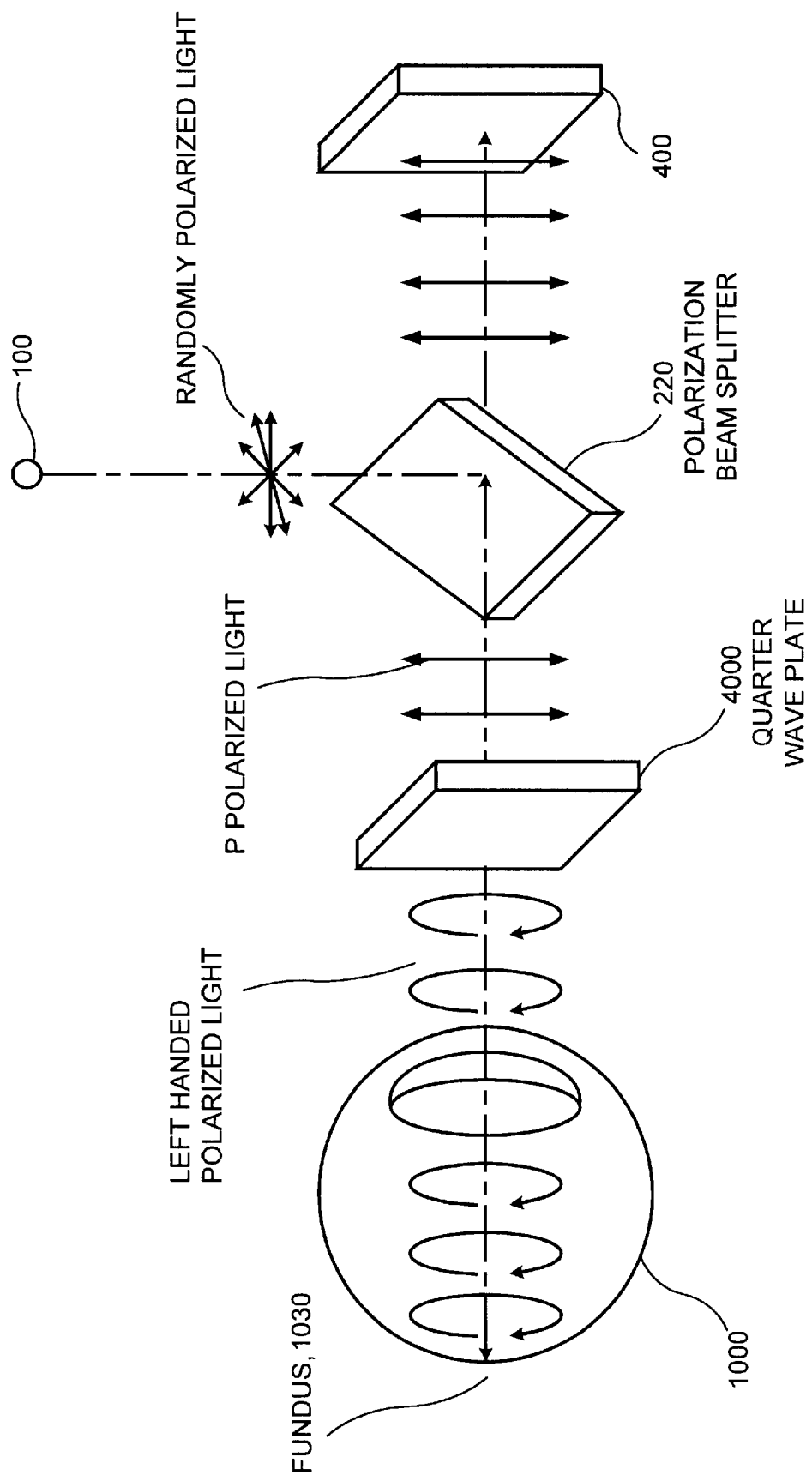
FIG. 3 is a diagrammatic view of assistance in explaining the principle of the ocular optical characteristic measuring apparatus shown in FIG. 1.
Figure 4:
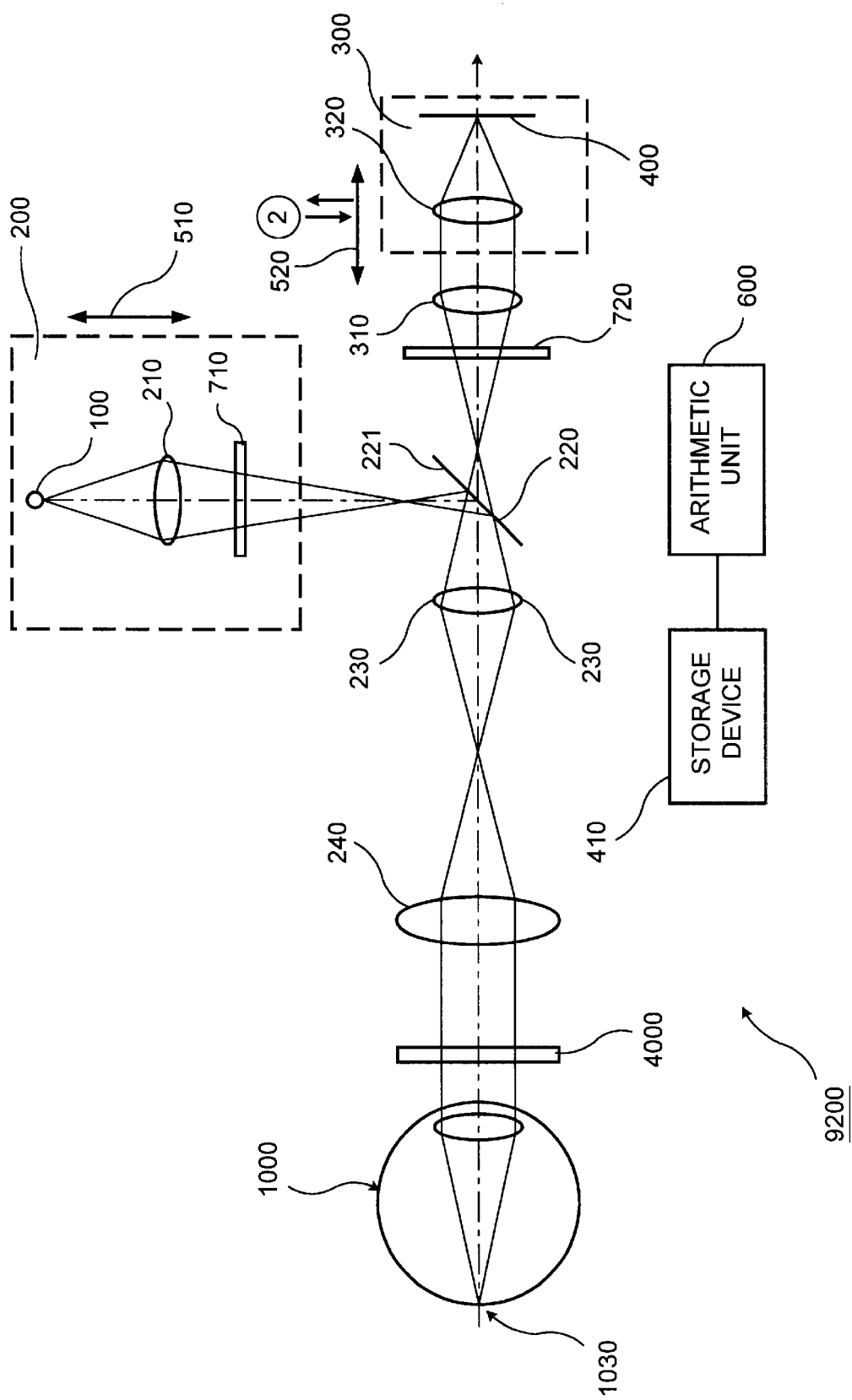
FIG. 4 is a diagrammatic view of the ocular optical characteristic measuring apparatus in the second embodiment.

FIG. 3 is a diagrammatic view of assistance in explaining the principle of the first embodiment and a light receiving method by which the ocular optical characteristic measuring apparatus 9100 receives reflected light reflected by the fundus 1030 of the eye. Regularly reflected light reflected by the fundus 1030 travels in left-handed polarized light through the quarter-wave plate 4000 again and is converted into P-polarized light. Then the P-polarized light travels through the polarization beam splitter 220 and fall on a photoelectric device 400.

The regularly reflected light regularly reflected by the fundus 1030 is able to fall on the photoelectric device 400. On the other hand, since scatter-reflected light scattered and reflected by the fundus 1030 is randomly polarized light, only a very small part, which is the same polarized light as the regularly reflected light reflected by the fundus 1030, of the randomly polarized light is able to reach the photoelectric device 400 and most part of the scatter-reflected light is cut.

First Embodiment

The ocular optical characteristic measuring apparatus 9100 in the first embodiment includes a light-projecting optical system 200 provided with a light source 100 and capable of projecting light emitted by the light source 100 on the fundus 1030 to form a target image on the fundus 1030, a light-receiving optical system 300 provided with the photoelectric device 400 on which a target image is formed by the light reflected by the fundus, and an arithmetic unit 600 capable of determining the optical characteristic of the eye 1000 on the basis of an image signal provided by the photoelectric device 400. The ocular optical characteristic measuring apparatus 9100 determines the ocular optical characteristic of the eye 1000 on the basis of a light-intensity distribution in a target image formed on the photoelectric device 400.

The ocular optical characteristic measuring apparatus 9100 includes further a polarization beam splitter 220 disposed in an optical passage for the light-projecting optical system 200 and the light-receiving optical system 300 to reflect only first linearly polarized light polarized in a first direction of polarization included in the light emitted by the light source 100 and transmits second linearly polarized light polarized in a second direction of polarization perpendicular to the first direction of polarization. Further the apparatus includes the quarter-wave plate 4000 disposed in an optical passage common to the light-projecting optical system 200 and the light-receiving optical system 300 and extending between the polarization beam splitter 220 and the eye 1000.

The light source 100 is a point-light source placed at a position corresponding to the focal point of a projection lens 210. The light source 100 is a laser light source that emits highly coherent light, a super luminescent diode (SLD) that emits light not as coherent as light emitted by a laser light source, or the like. The light source 100 emits light having random polarized components.

The light-projecting optical system 200 includes the projection lens 210, the polarization beam splitter 220, a relay lens 230, an objective 240 and the quarter-wave plate 4000.

Light emitted by the light source 100 travels through the projection lens 210 and the relay lens 230 to the objective 240. The objective 240 collimates light emitted by the light source 100 and projected through the projection lens 210 to form an image on the fundus 1030 of the eye 1000.

The polarization beam splitter 220 reflects the light projected through the projection lens 210 toward the objective 240. The polarization beam splitter 220, which is capable of converting light into linearly polarized light, is placed in a common optical passage for both the light-projecting optical system 200 and the light-receiving optical system 300. The polarization beam splitter 220 reflects S-polarized light. The polarization beam splitter 220 reflects only first linearly polarized light polarized in a first direction of polarization, i.e., S-polarized light, included in randomly polarized light emitted by the light source 100 and transmits second linearly polarized light polarized in a second direction of polarization perpendicular to the first direction of polarization, i.e., P-polarized light.

The quarter-wave plate 4000 is disposed in the optical passage common to the light-projecting optical system 200 and the light-receiving optical system 300 and extending between the polarization beam splitter 220 and the eye 1000. The quarter-wave plate 4000 is set at an azimuth angle of +45° to the S-polarized light (right-handed polarized light).

Regularly reflected light regularly reflected by the fundus 1030 is left-handed polarized light and becomes P-polarized light after passing the quarter-wave plate 4000 again. The P-polarized light travels through the polarization beam splitter 220 and falls on the photoelectric device 400. Thus, all the regularly reflected light reflected by the fundus 1030 falls on the photoelectric device 400. On the other hand, scatter-reflected light scattered and reflected by the fundus 1030 is randomly polarized light. Therefore, only a very small part, which is the same polarized light as the regularly reflected light, of the randomly polarized light is able to reach the photoelectric device 400 and most part of the scatter-reflected light is cut.

Thus the scatter-reflected light scattered and reflected by the fundus 1030 and converted into randomly polarized light excluding only a small part thereof is unable to fall on the photoelectric device 400. A target image is formed on the photoelectric device 400 substantially only by the regularly reflected light; that is the substantially all the scatter-reflected light is eliminated before the reflected light reflected by the fundus 1030 reaches the photoelectric device 400.

Although first embodiment employs the polarization beam splitter 220 that reflects S-polarized light, the polarization beam splitter 220 may be such as reflects P-polarized light.

The light-receiving optical system 300 includes the objective 240, the relay lens 230, the polarization beam splitter 220, a collimator lens 310 and a focusing lens 320.

The collimator lens 310 collimates the reflected light reflected by the fundus 1030 in parallel light rays before the reflected light reaches the focusing lens 320. The focusing lens 320 focuses the reflected light reflected by the fundus 1030 on the photoelectric device 400. The photoelectric device 400, i.e., a light-receiving device, employed in the first embodiment is an imaging device, such as a CCD. The photoelectric device 400 is not limited to a CCD and may be any imaging device, provided that the imaging device is able to convert an optical image into an electric image signal. Image signals formed on the photoelectric device 400 are stored in a storage device 410. The storage device 410 is a frame memory.

The light source 100 and the fundus 1030 are conjugate, and the fundus 1030 and the photoelectric device 400 are conjugate.

A projection lens moving mechanism 510 is a focusing mechanism that moves the projection lens 210 for focusing. Similarly, a focusing lens driving mechanism 520 is a focusing mechanism that moves the focusing lens 320 for focusing. The projection lens moving mechanism 510 and the focusing lens driving mechanism 520 are provided with movement measuring devices, such as encoders, to measure the respective displacements of the projection lens 210 and the focusing lens 320.

The ocular optical characteristic measuring apparatus in the first embodiment is provided with a projection lens controller that controls and supplies power to the projection lens moving mechanism 510 on the basis of control signals provided by the arithmetic unit 600, and a focusing lens controller that controls and supplies power to the focusing lens driving mechanism 520 on the basis of control signals provided by the arithmetic unit 600.

The target image formed on the fundus 1030 by the ocular optical characteristic measuring apparatus in the first embodiment is a light spot. A slit image or an edge image may be used instead of the light spot. The shape of the target image may be that of a pinhole, a ring or any suitable figure.

The arithmetic unit 600 controls the general operations of the ocular optical characteristic measuring apparatus 9100, successively determines the respective displacements of the projection lens 210 moved by the projection lens moving mechanism 510 and the focusing lens 320 moved by the focusing lens driving mechanism 520, and stores image signals representing images formed on the photoelectric device 400 in the storage device 410. The arithmetic unit 600 executes operations on the basis of the positions of the projection lens 210 and the focusing lens 320, and the corresponding image signals stored in the storage device 410.

The ocular optical characteristic measuring apparatus eliminates substantially all the scatter-reflected light scattered and reflected by the fundus 1030 and guides only the regularly reflected light regularly reflected by the fundus 1030 to the photoelectric device 400 to eliminate an aberration component caused by the blurring effect of the fundus 1030.

After the regularly reflected light has been focused on the photoelectric device 400, two-dimensional intensity distribution I(x, y) in the least circle of confusion is measured, and the arithmetic unit 600 calculates a point spread function P(x, y) representing the optical characteristic of the ocular optical system of the eye 1000 from the two-dimensional intensity distribution I(x, y).

The operation of the arithmetic unit 600 will be more specifically described. The two-dimensional intensity distribution I(x, y) in the target image formed on the photoelectric device 400 is expressed by the superposition integration of a point spread function P(x, y) expressing the optical characteristic of the ocular optical system from a cornea to the fundus 1030 and a point spread function P(−x, −y) expressing the optical characteristic of the ocular optical system from the fundus 1030 to the cornea. In the following expression, the target image is supposed to be a pinhole image.

$$I(x, y) = P(x, y) * P(-x, -y) \tag{1}$$

where "*" indicates superposition integration (FT).

Expression (2) is obtained by subjecting Expression (1) to Fourier transformation.

$$FT[I(x, y)] = FT[P(x, y) \cdot FT[P(-x, -y)] \tag{2}$$
$$= (FT[P(x, y)])^2$$

Therefore, $$FT[P(x, y)] = (FT[I(x, y)])^{1/2} \tag{3}$$

Expression (4) is obtained by subjecting Expression (3) to inverse Fourier transformation (IFT).

$$P(x, y) = IFT((FT[I(x, y)])^{1/2}) \tag{4}$$

The two-dimensional intensity distribution I(x, y) in the target image formed on the photoelectric device 400 is determined, and the point spread function P for the ocular optical system of the eye 1000 can be determined according to the Expression 4.

Since the polarized component of the reflected light regularly reflected by each surface of a lens system between the polarization beam splitter 220 and the quarter-wave plate 4000 disposed in front of the eye 1000 is stored, detrimental reflected light is reflected by the polarization beam splitter 220 so that the detrimental reflected light may not reach the photoelectric device 400 and, consequently, the accurate measurement of the light intensity distribution in the target image can be improved.

Although the quarter-wave plate 4000 included in the first embodiment is set at an azimuth angle of +45° to the S-polarized light to project right-handed polarized light on the fundus 1030 of an eye 1000, the same may be set at an azimuth angle of −45° to the S-polarized light to project left-handed polarized light. If the quarter-wave plate 4000 is set at an azimuth angle of −45° to the S-polarized light, the regularly reflected light regularly reflected by the fundus 1030 is right-handed polarized light and is converted into P-polarized light through the quarter-wave plate 4000 again.

Second Embodiment

An ocular optical characteristic measuring apparatus 9200 in a second embodiment according to the present invention includes a light-projecting optical system 200 provided with a light source 100 and capable of projecting light emitted by the light source 100 on the fundus 1030 of an eye 1000 to form a target image on the fundus 1030, a light-receiving optical system 300 provided with a photoelectric device 400 and capable of forming a target image on the photoelectric device 400, and an arithmetic unit 600 capable of determining the optical characteristic of the eye 1000 on the basis of an image signal provided by the photoelectric device 400. The ocular optical characteristic measuring apparatus 9200 determines the ocular optical characteristic of the eye 1000 on the basis of a light-intensity distribution in the target image formed on the photoelectric device 400.

The ocular optical characteristic measuring apparatus 9200 includes further a first polarizing plate 710 included in the light-projecting optical system 200, a second polarizing plate 720 included in the light-receiving optical system 300, a beam splitter 221 disposed in an optical passage common to the light-projecting optical system 200 and the light-receiving optical system 300, and a quarter-wave plate 4000 disposed in an optical passage common to the light-projecting optical system 200 and the light-receiving optical system 300 and extending between the beam splitter 220 and the eye 1000.

The light-projecting optical system 200 includes a projection lens 210, the first polarizing plate 710, the beam splitter 221, a relay lens 230, an objective 240 and the quarter-wave plate 4000.

The beam splitter 221 reflects light emitted by a light source 100, traveled through the projection lens 210 and fallen thereon toward the objective 240. The beam splitter 221 employed in the second embodiment, which differ from the polarization beam splitter 220 employed in the first embodiment, is incapable of polarizing function.

The first polarizing plate 710 included in the light-projecting optical system 200 transmits only first linearly polarized light polarized in a first direction of polarization, i.e., S-polarized light, included in randomly polarized light emitted by a light source 100.

The second polarizing plate 720 associated with the light-receiving optical system 300 is disposed between the beam splitter 221 and the photoelectric device 400. The second polarizing plate 720 transmits only second linearly polarized light polarized in a second direction of polarization (P polarized light) perpendicular to the first direction of polarization, i.e., S-polarized light.

Only the first linearly polarized light, i.e., the S-polarized light, included in the light emitted by the light source 100 travels through the first polarizing plate 710, is reflected by the beam splitter 221 toward the quarter-wave plate 4000. The quarter-wave plate 4000 is set at an azimuth angle of +45° to the S-polarized light to project right-handed polarized light on the fundus 1030 of an eye 1000.

Regularly reflected light regularly reflected by the fundus 1030 is left-handed polarized light and becomes P-polarized light after passing the quarter-wave plate 4000. The P-polarized light travels through the beam splitter 221 and falls on the second polarizing plate 720. The second polarizing plate 720 transmits only the second linearly polarized light, i.e., P-polarized light, and the second polarized light falls on the photoelectric device 400.

Thus, all the regularly reflected light regularly reflected by the fundus 1030 falls on the photoelectric device 400. On the other hand, scatter-reflected light scattered and reflected by the fundus 1030 is randomly polarized light. Therefore, only a very small part, which is the same polarized light as the regularly reflected light, of the randomly polarized light is able to reach the photoelectric device 400 and most part of the scatter-reflected light is cut.

Thus the scatter-reflected light scattered and reflected by the fundus 1030 and converted into randomly polarized light excluding only a small part thereof is unable to fall on the photoelectric device 400. A target image is formed on the photoelectric device 400 substantially only by the regularly reflected light.

Since the polarized component of the reflected light regularly reflected by each surface of a lens system between the beam splitter 221 and the quarter-wave plate 4000 disposed in front of the eye 1000 is stored in the second embodiment described above, detrimental reflected light is reflected by the second polarizing plate 720 so that the detrimental reflected light may not reach the photoelectric device 400 and, consequently, the accurate measurement of the light intensity distribution in the target image can be achieved.

The ocular optical characteristic measuring apparatus in the second embodiment is the same in other respects as that in the first embodiment and the further description thereof will be omitted.

Although the first polarizing plate 710 included in the second embodiment is a linear-polarizing plate that transmits only S-polarized light, the first polarizing plate 710 may be a linear-polarizing plate that transmits only P-polarized light, provided that the respective directions of polarization of the first polarizing plate 710 and the second polarizing plate 720 are perpendicular to each other.

If a light source that emits a linearly polarized light is used as the light source 100, the first polarizing plate 710 may be omitted. When such a light source is employed, the direction of polarization of the second polarizing plate 720 must be perpendicular to the direction of polarization of the light emitted by the light source 100.

The ocular optical characteristic measuring apparatus according to the present invention forms a target image on the fundus by projecting light emitted by the light source by the light-projecting optical system, guides reflected light reflected by the fundus and forming a target image to the photoelectric device by the light-receiving optical system, and determines the ocular optical characteristic of the eye on the basis of signals provided by the photoelectric device and indicating a light intensity distribution in the target image formed on the photoelectric device. Scatter-reflected light scattered and reflected by the blurring effect of the fundus is eliminated and only regularly reflected light falls on the photoelectric device to form the target image only by the regularly reflected light on the photoelectric device. Thus the optical characteristic of the ocular optical system from the cornea to the fundus can be accurately measured without being affected by the effect of unmeasurable blurred reflection particular to the eye.

What is claimed is:

1. An ocular optical characteristic measuring apparatus comprising:
    a light-projecting optical system including a light source unit and capable of projecting a target image on a fundus of an eye;
    a light-receiving optical system including a photoelectric device and capable of guiding reflected light reflected by the fundus to the photoelectric device; and
    an arithmetic unit capable of determining a light intensity distribution in the target image formed on the photoelectric device on the basis of an image signal provided by the photoelectric device and of estimating optical characteristic of the eye from the light intensity distribution in the target image;
    wherein substantially all scatter-reflected light included in the reflected light reflected by the fundus is eliminated, and only the reflected light substantially not including scatter-reflected light is guided to the photoelectric device.

2. An ocular optical characteristic measuring apparatus comprising:
    a light-projecting optical system including a light source unit and capable of projecting a target image on a fundus of an eye;
    a light-receiving optical system including a photoelectric device and capable of guiding reflected light reflected by the fundus to the photoelectric device; and
    an arithmetic unit capable of determining a light intensity distribution in the target image formed on the photoelectric device on the basis of an image signal provided by the photoelectric device and of estimating optical characteristic of the eye from the light intensity distribution in the target image;
    wherein a polarization beam splitter capable of reflecting first linearly polarized light polarized in a first direction of polarization and included in the light emitted by the light source unit and of transmitting second linearly polarized light polarized in a second direction of polarization perpendicular to the first direction of polarization is disposed in an optical passage common to the light-projecting optical system and the light-receiving optical system, and a quarter-wave plate is disposed at a position between the polarization beam splitter and the eye on an optical passage common to the light-projecting optical system and the light-receiving optical system.

3. An ocular optical characteristic measuring apparatus comprising:
    a light-projecting optical system including a light source unit and capable of projecting a target image on a fundus of an eye;
    a light-receiving optical system including a photoelectric device and capable of guiding reflected light reflected by the fundus to the photoelectric device; and
    an arithmetic unit capable of determining a light intensity distribution in the target image formed on the photoelectric device on the basis of an image signal provided by the photoelectric device and of estimating optical characteristic of the eye from the light intensity distribution in the target image;
    wherein the light-projecting optical system is provided with a first polarizing plate capable of transmitting only first linearly polarized light polarized in a first direction of polarization included in the light emitted by the light source unit, a beam splitter is disposed on an optical passage common to the light-projecting optical system and the light-receiving optical system to guide the first linearly polarized light transmitted by the first polarizing plate toward the eye, a quarter-wave plate is disposed at a position between the beam splitter and the eye on an optical passage common to the light-projecting optical system and the light-receiving optical system, and the light-receiving optical system is provided with a second polarizing plate capable of transmitting only second linearly polarized light polarized in a second direction of polarization perpendicular to the first direction of polarization and disposed in an optical passage between the beam splitter and the photoelectric device.

4. An ocular optical characteristic measuring apparatus comprising:
    a light-projecting optical system including a light source unit and capable of projecting a target image on a fundus of an eye;

a light-receiving optical system including a photoelectric device and capable of guiding reflected light reflected by the fundus to the photoelectric device; and an arithmetic unit capable of determining a light intensity distribution in the target image formed on the photoelectric device on the basis of an image signal provided by the photoelectric device and of estimating optical characteristic of the eye from the light intensity distribution in the target image;

wherein the light source unit is provided with a light source capable of emitting first linearly polarized light polarized in a first direction of polarization, a beam splitter is disposed on an optical passage common to the light-projecting optical system and the light-receiving optical system to guide the light emitted by the light source unit toward the eye, a quarter-wave plate is disposed at a position between the beam splitter and the eye on an optical passage common to the light-projecting optical system and the light-receiving optical system, and the light-receiving optical system is provided with a second polarizing plate capable of transmitting only linearly polarized light polarized in a second direction of polarization perpendicular to the first direction of polarization and disposed in an optical passage between the beam splitter and the photoelectric device.

* * * * *